United States Patent [19]
Xiang et al.

[11] Patent Number: 6,100,259
[45] Date of Patent: Aug. 8, 2000

[54] CANNABINOID RECEPTOR MODULATORS

[75] Inventors: Jia-Ning Xiang; John Duncan Elliott, both of Wayne, Pa.; Steven Todd Atkinson, Fishers, Ind.; Siegfried Benjamin Christensen, IV, Philadelphia, Pa.

[73] Assignee: SmithKline Beecham Corporation, Philadelphia, Pa.

[21] Appl. No.: 09/355,151

[22] PCT Filed: Jan. 20, 1998

[86] PCT No.: PCT/US98/01175

§ 371 Date: Oct. 15, 1999

§ 102(e) Date: Oct. 15, 1999

[87] PCT Pub. No.: WO98/31227

PCT Pub. Date: Jul. 23, 1998

Related U.S. Application Data

[60] Provisional application No. 60/035,073, Jan. 21, 1997.
[51] Int. Cl.[7] .......................... A61K 31/535; A61P 19/02; C07D 413/12
[52] U.S. Cl. ....................... 514/236.5; 544/132; 544/137; 544/138; 544/140; 544/371; 546/211; 546/275.4
[58] Field of Search ............................. 544/140; 546/211; 514/236.5

[56] References Cited

U.S. PATENT DOCUMENTS 5,462,960  10/1995  Barth et al. .
5,948,777   9/1999  Bender et al. .......................... 544/140

FOREIGN PATENT DOCUMENTS

WO 93/25535  12/1993  WIPO .

*Primary Examiner*—Robert W. Ramsuer
*Attorney, Agent, or Firm*—Soma G. Simon; William T. King; Charles M. Kinzig

[57] ABSTRACT

Novel pyrazole derivatives are provided which are cannabinoid receptor modulators.

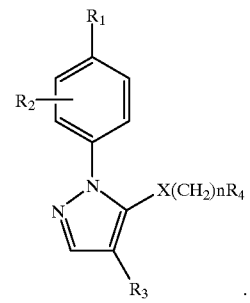

13 Claims, No Drawings

CANNABINOID RECEPTOR MODULATORS

This application is a 371 of PCT/US98/01175 filed Jan. 20, 1998, which claims the benefit of provisional application 60/035,073 filed Jan. 21, 1997.

FIELD OF THE INVENTION

The present invention relates to novel pyrazole derivatives, pharmaceutical compositions containing these compounds and their use in the treatment of diseases connected with the modulation of the cannabinoid peripheral receptor.

BACKGROUND OF THE INVENTION

Cannabinoids are a specific class of psychoactive compounds present in Indian cannabis (*Cannabis sativa*), including about sixty different molecules, the most representative being cannabinol, cannabidiol and several isomers of tetrahydrocannabinol. Knowledge of the therapeutic activity of cannabis dates back to the ancient dynasties of China, where, 5,000 years ago, cannabis was used for the treatment of asthma, migraine and some gynaecological disorders. These uses later became so established that, around 1850, cannabis extracts were included in the US Pharmacopaeia and remained there until 1947.

Cannabinoids are known to cause different effects on various systems and/or organs, the most important being on the central nervous system and on the cardiovascular system. These effects include alterations in memory and cognition, euphoria, and sedation. Cannabinoids also increase heart rate and vary systemic arterial pressure. Peripheral effects related to bronchial constriction, immunomodulation, and inflammation have also been observed. The capability of cannabinoids to reduce intraocular pressure and to affect respiratory and endocrine systems is also well documented. See e.g. L. E. Hollister, Health Aspects of Cannabis, *Pharmacological Reviews*, Vol. 38, pp. 1–20, (1986). More recently, it was found that cannabinoids suppress the cellular and humoral immune responses and exhibit antiinflammatory properties. Wirth et al., Antiinflammatory Properties of Cannabichrome, *Life Science*, Vol. 26, pp. 1991–1995, (1980).

In spite of the foregoing benefits, the therapeutic use of cannabis is controversial, both due to its relevant psychoactive effects (causing dependence and addiction), and due to manifold side effects that have not yet been completely clarified. Although work in this field has been ongoing since the 1940's, evidence indicating that the peripheral effects of cannabinoids are directly mediated, and not secondary to a CNS effect, has been limited by the lack of receptor characterization, the lack of information concerning an endogenous cannabinoid ligand and, until recently, the lack of receptor subtype selective compounds.

The first cannabinoid receptor was found to be mainly located in the brain, in neural cell lines, and, only to a lesser extent, at the peripheral level. In view of its location, it was called the central receptor ("CB1"). See Matsuda et al., "Structure of a Cannabinoid Receptor and Functional Expression of the Cloned CDNA," *Nature*, Vol. 346, pp. 561–564 (1990. The second cannabinoid receptor ("CB2") was identified in the spleen, while being absent at the central location, and was assumed to modulate the non psychoactive effects of the cannabinoids. See Munro et el., "Molecular Characterization of a Peripheral Receptor for Cannabinoids," *Nature*, Vol. 365, pp. 61–65 (1993).

Recently, some compounds have been prepared which are capable of acting as agonists on both the cannabinoid receptors. For example, use of derivatives of dihydroxypyrrole-(1,2,3-d,e)-1,4-benzoxazine in the treatment of glaucoma and the use of derivatives of 1,5-diphenyl-pyrazole as immunomodultors or psychotropic agents in the treatment of various neuropathologies, migraine, epilepsy, glaucoma, etc are known. See U.S. Pat. No. 5,112,820 and EP 576357, respectively. However, because these compounds are active on both the CB1 and CB2 receptor, they can lead to serious psychoactive effects.

The foregoing indications and the preferential localization of the CB2 receptor in the immune system confirms a specific role of CB2 in modulating the immune and antiinflammatory response to stimuli of different sources.

The role of CB2 in immunomodulation, inflammation, osteoporosis, cardiovascular, renal and other disease conditions is now being examined. In light of the fact that cannabinoids act on receptors capable of modulating different functional effects, and in view of the low homology between CB2 and CB1, the importance of developing a class of drugs selective for the specific receptor sub-type is evident. The natural or synthetic cannabinoids currently available do not fulfill this function because they are active on both receptors.

Based on the foregoing, there is a need for compounds which are capable of selectively modulating the peripheral receptor for cannabinoids and, therefore, the pathologies associated with such receptors. Thus, CB2 modulators offer a unique approach toward the pharmacotherapy of immune disorders, inflammation, osteoporosis, renal ischemia and other pathophysiological conditions.

SUMMARY OF THE INVENTION

The present invention provides novel pyrazole derivatives represented by Formula (I) and pharmaceutical compositions containing these compounds, and their use as CB2 receptor modulators which are useful in the treatment of a variety of diseases including but not limited to immune disorder, inflammation, osteoporosis and renal ischemia.

The present invention further comprises a method for modulating CB2 receptors in an animal, including humans, which comprises administering to an animal in need thereof an effective amount of a compound of Formula (I).

DETAILED DESCRIPTION OF THE INVENTION

The compounds of the present invention are represented by structural Formula (I):

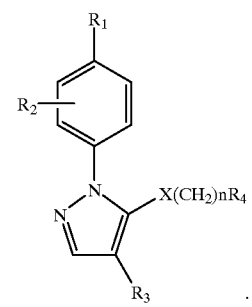

wherein:

$R_1$ is $OCH_3$, Br, isopropyl, or Ar;

$R_2$ is H, OH, $C_{1-5}$alkoxy, $C_{1-5}$alkyl, $N(R_5)_2$, $NO_2$, Br, F, I, Cl, $CF_3$, or $X(C(R_5)_2)OR_5$;

$R_3$ is hydrogen, $(CH_2)_nXR_5$, $C(O)R_5$, $CO_2R_5$, $CON(R_5)_2$, oxazolinyl, oxazolyl, thiazolyl, pyrazolyl, triazolyl, imidazolyl, tetrazolyl, imidazolinyl, thiazolinyl, isoxazolyl, oxadiazolyl, or thiadiazolyl, each of these heterocyclic rings being unsubstituted or substituted by one or two $C_{1-3}$ alkyl or fluoroalkyl groups;

$R_4$ is morpholinyl, piperazinyl or piperidinyl, each moiety being unsubstituted or substituted by one or two $C_{1-5}$ alkyl, OH, $NO_2$ or $N(R_5)_2$ groups;

$R_5$ is hydrogen or $C_{1-8}$ alkyl;

X is O or $NR_5$;

Ar is phenyl, anthracenyl, naphthyl, indolyl, pyridinyl, thiophenyl, thiazolyl, isothiazolyl, triazolyl, tetrazolyl, imidazolyl, oxadiazolyl, pyrrolyl or pyrimidinyl; each moiety being unsubstituted or substituted by one or two Z groups;

Z is H, OH, $CO_2R_5$, $C_{1-10}$alkoxy, $C_{1-5}$alkyl, $N(R_5)_2$, $NO_2$, Br, F, I, Cl, $CF_3$, or $X(CH_2)_nOR_5$; and n is 1 to 6;

provided that when n is 1, $R_5$ is not hydrogen in $X(CH_2)_nOR_5$.

Also included in the present invention are pharmaceutically acceptable salt complexes. Preferred are the ethylene diamine, sodium, potassium, calcium and ethanolamine salts.

All alkyl and alkoxy groups may be straight or branched. The compounds of the present invention may contain one or more asymmetric carbon atoms and may exist in racemic and optically active forms. All of these compounds and diastereomers are contemplated to be within the scope of the present invention.

In preferred compounds of the present invention:

$R_1$ is $C_{1-5}$ alkyl or Ar;

$R_2$ is hydrogen, $C_{1-5}$ alkyl or Ar;

$R_3$ is selected from the group consisting of $CO_2R_5$, oxazolinyl, tetrazolyl, and oxazolyl, unsubstituted or substituted by one or two $C_{1-2}$ alkyl or fluoroalkyl groups;

$R_4$ is morpholinyl, piperazinyl or piperidinyl, unsubstituted or substituted by one or two $C_{1-5}$ alkyl groups;

$R_5$ is $C_{1-5}$ alkyl;

X is O;

Ar is phenyl, unsubstituted or substituted by one or two Z groups; and n is 2.

In more preferred compounds of the present invention:

$R_1$ is isopropyl or phenyl, substituted by dichloro, CHO, $OCH_2OCH_3$; and $R_5$ is methyl or ethyl.

Preferred compounds useful in the present invention include ethyl 5-(2-morpholin-4-ylethoxy)-1-(4-naphthylphenyl)pyrazole-4-carboxylate, ethyl 5-(2-morpholin-4-ylethoxy)-1-(2-methyl(4-naphthylphenyl))pyrazole-4-carboxylate, 5-(2-morpholin-4-ylethoxy)-1-(4-isopropylphenyl)pyrazole-4-(1-methyl)-tetrazole, 5-(2-morpholin-4-ylethoxy)-1-(4-isopropylphenyl)pyrazole-4-(2-methyl)-tetrazole, ethyl 5-(2-morpholin-4-ylethoxy)-1-(4-(2-formylphenyl)phenyl)pyrazole-4-carboxylate, ethyl 5-(2-morpholin-4-ylethoxy)-1-(4-(2-methoxymethoxyphenyl)phenyl)-pyrazole-4-carboxylate, ethyl 5-(2-morpholin-4-ylethoxy)-1-(4-(2-hydroxyphenyl)phenyl)pyrazole-4-carboxylate, ethyl 5-(2-morpholin-4-ylethoxy)-1-(4-(2,6-dimethylphenyl)phenyl)pyrazole-4-carboxylate; ethyl 5-(2-morpholin-4-ylethoxy)-1-(4-(2,6-dichlorophenyl)phenyl)pyrazole-4-carboxylate, ethyl 5-(2-morpholin-4-ylethoxy)-1-(4-(2-(2-methylpropanyl)phenyl)phenyl)-pyrazole-4-carboxylate, ethyl 5-(2-morpholin4-ylethoxy)-1-(4-(2-propoxyphenyl)phenyl)pyrazole-4-carboxylate, ethyl 5-(2-morpholin-4-ylethoxy)-1-(4-(2-hydroxymethylphenyl)phenyl)pyrazole-4-carboxylate, ethyl 5-(2-morpholin-4-ylethoxy)-1-(4-(2-ethoxyphenyl)phenyl) pyrazole-4-carboxylate; 5-(2-morpholin-4-ylethoxy)-1-(4-isopropylphenyl)pyrazole-4-oxazoline, ; 5-(2-morpholin-4-ylethoxy)-1-(4-isopropylphenyl)pyrazole-4-(5-methyl) oxazoline, ethyl 5-(2-morpholin-4-ylethoxy)-1-(4-(2-hydroxyethoxyphenyl)phenyl)-pyrazole-4-carboxylate, ethyl 5-(2-morpholin-4-ylethoxy)-1-(4-(2-nitrophenyl) phenyl)pyrazole-4-carboxylate, ethyl 5-(2-morpholin-4-ylethoxy)-1-(4-(2-acetoxynitrilephenyl)phenyl)pyrazole-4-carboxylate, ethyl 5-(2-morpholin-4-ylethoxy )-1-(4-(2,3-dichlorophenyl)phenyl)pyrazole-4-carboxylate, 5-(2-morpholin-4-ylethoxy)-1-(4-isopropylphenyl)pyrazole-4-(1-ethyl)-tetrazole and 5-(2-morpholin-4-ylethoxy)-1-(4-isopropylphenyl)pyrazole-4-(2-ethyl)-tetrazole, 5-(2-morpholin-4-ylethoxy)-1-(4-isopropylphenyl)pyrazole-4-carboxylic acid, 5-(2-morpholin-4-ylethoxy)-1-(4-isopropylphenyl)pyrazol-4-yl methanol, 5-(2-morpholin-4-ylethoxy)-1-(4-isopropylphenyl)pyrazole-4-N,N-dimethylcarbamidate, 5-(2-morpholin-4-ylethoxy)-1-(4-isopropylphenyl)pyrazole-4-carbamide, (+/-)-ethyl 5-((1-methyl-2-piperidinyl)methoxy)-1-(4-isopropylphenyl) pyrazole-4-carboxylate, 5-(2-morpholin-4-ylethoxy)-1-(4-isopropylphenyl)pyrazole, 5-(2-morpholin-4-ylethoxy)-1-(4-isopropylphenyl)pyrazole-4-methyl, ethyl 5-(2-morpholin-4-ylethoxy)-1-(4-(3,5-bis(trifluoromethyl)phenyl)-phenyl)pyrazole-4-carboxylate, ethyl 5-(2-morpholin-4-ylethoxy)-1-(4-phenylphenyl)pyrazole-4-carboxylate, ethyl 5-(2-morpholin-4-ylethoxy)-1-(4-(3,5-dichlorophenyl)phenyl)pyrazole-4-carboxylate, ethyl 5-(2-morpholin-4-ylethoxy)-1-(4-(3-chlorophenyl)phenyl) pyrazole-4-carboxylate, ethyl 5-(2-morpholin-4-ylethoxy)-1-(4-(4-chlorophenyl)phenyl)pyrazole-4-carboxylate, ethyl 5-(2-morpholin-4-ylethoxy)-1-(4-(4-formylphenyl)phenyl) pyrazole-4-carboxylate, ethyl 5-(2-morpholin-4-ylethoxy)-1-(4-(2,4-dichlorophenyl)phenyl)pyrazole-4-carboxylate, ethyl 5-(2-morpholin-4-ylethoxy)-1-(4-(4-methoxyphenyl)phenyl)pyrazole-4-carboxylate, ethyl 5-(2-morpholin-4-ylethoxy)-1-(4-(4 -methylphenyl)phenyl)pyrazole-4-carboxylate, ethyl 5-(2-morpholin-4-ylethoxy)-1-(4-(3-aminophenyl)phenyl)pyrazole-4-carboxylate, 5-(2-morpholin-4-ylethoxy)-1-(4-(4-carboxyphenyl)phenyl)pyrazole-4-carboxylic acid, methyl 5-(2-morpholin-4-ylethoxy)-1-(4-(4-methoxycarbonylphenyl)-phenyl) pyrazole-4-carboxylate, ethyl 5-(2-morpholin-4-ylethoxy)-1-(4-(2-N-diethylacetamidephenyl)-phenyl)pyrazole-4-carboxylate, ethyl 5-(2-morpholin-4-ylethoxy)-1-(4-(2-octoxyphenyl)phenyl)pyrazole-4-carboxylate, ethyl 5-(2-morpholin-4-ylethoxy)-1-(4-(2-tert-butyloxycarbomethoxyphenyl)-phenyl)pyrazole-4-carboxylate, ethyl 5-(2-morpholin-4-ylethoxy)-1-(4-(2-benzyloxyphenyl)phenyl)pyrazole-4-carboxylate, 5-(2-morpholin-4-ylethoxy)-1-(4-isopropylphenyl)pyrazole-4-methyl ketone, 5-(2-morpholin-4-ylethoxy)-1-(4-isopropylphenyl)pyrazol-4-yl-N-ethylcarboxamide, ethyl 5-(2-morpholin-4-ylethoxy)-1-(4-(2-carbomethoxyphenyl) phenyl)pyrazole-4-carboxylate, ethyl 5-(2-morpholin-4-ylethoxy)-1-(4-anthracenylphenyl)pyrazole-4-carboxylate, ethyl 5-(2-morpholin-4-ylethoxy)-5-(4-(2-n-butoxyphenyl) phenyl)pyrazole-4-carboxylate, ethyl 5-(2-morpholin-4-ylethoxy)-1-(4-(2-methoxyethoxyphenyl)phenyl)-pyrazole-4-carboxylate, methyl 5-(2-morpholin -4-ylethoxy)-1-(4- isopropylphenyl)pyrazole-4-carboxylate, isopropyl 5-(2-morpholin-4-ylethoxy)-1-(4-isopropylphenyl)pyrazole-4-carboxylate, propyl 5-(2-morpholin-4-ylethoxy)-1-(4-isopropylphenyl)pyrazole-4-carboxylate, ethyl 5-(2-pyridinylmethoxy)-1-(4-isopropylphenyl)pyrazole-4-carboxylate, (R)-(−)-5-(2-morpholin-4-ylethoxy)-1-[4-(2,6-dichlorophenyl)phenyl]pyrazole-4-(5-methyl)oxazoline, (S)-(+)-5-(2-morpholin-4-ylethoxy)-1-[4-(2,6-dichlorophenyl)phenyl]pyrazole-4-(5-methyl)oxazoline, 5-(2-morpholin-4-ylethoxy)-1-(4-isopropylphenyl) pyrazole-4-(2-methyl)oxadiazole, 4-methoxymethyl-5-(2-morpholin-4-ylethoxy)-1-(4-(2-methylnaphthyl)phenyl) pyrazole, 5-(2-morpholin-4-ylethoxy)-1-(4-(2,6-dichlorophenyl)phenyl)pyrazole, 5-(2-morpholin-4-ylethoxy)-1-(4-(2,3-dichlorophenyl)phenyl)pyrazole, 5-(2-morpholin-4-ylethoxy)-1-(4-isopropylphenyl)pyrazole-4-nitrile, 5-(2-morpholin-4-ylethoxy)-1-(4-isopropylphenyl) pyrazole-4-tetrazole, ethyl 5-(4-pyridinylmethoxy)-1-(4-isopropylphenyl)pyrazole-4-carboxylate, ethyl 5-(2-morpholin-4-ylethoxy)-1-(4-isopropylphenyl)pyrazole-4-carboxylate, 5-(2-morpholin-4-ylethoxy)-1-(4-isopropylphenyl)pyrazole-4-tetrazole, 5-(2-morpholin-4-ylethoxy)-1-(4-isopropylphenyl)pyrazole4(1-methyl)-tetrazole, 5-(2-morpholin-4-ylethoxy)-1-(4-isopropylphenyl)pyrazole-4-(2-methyl)-tetrazole, ethyl 5-(4-pyridinylmethoxy)-1-(4-isopropylphenyl)pyrazole-4-carboxylate, ethyl 5-(2-morpholin-4-ylethoxy)-1-(4 -isopropylphenyl)pyrazole-4-carboxylate, 5-(2-morpholin-4-ylethoxy)-1-[4-(2,6-dichlorophenyl)phenyl]pyrazole-4-(1-ethyl)-tetrazole, and 5-(2-morpholin-4-ylethoxy)-1-[4-(2, 6-dichlorophenyl)phenyl]pyrazole-4-(2-ethyl)-tetrazole.

More preferred compounds useful in the present invention include ethyl 5-(2-morpholin-4-ylethoxy)-1-(4-(2-formylphenyl)phenyl)pyrazole-4-carboxylate, ethyl 5-(2-morpholin-4-ylethoxy)-1-(4-(2-methoxymethoxyphenyl) phenyl)-pyrazole-4-carboxylate, ethyl 5-(2-morpholin-4-ylethoxy)-1-(4-(2-hydroxyphenyl)phenyl)pyrazole-4-carboxylate, ethyl 5-(2-morpholin-4-ylethoxy)-1-(4-(2,6-dimethylphenyl)phenyl)pyrazole-4-carboxylate; ethyl 5-(2-morpholin-4-ylethoxy)-1-(4-(2,6-dichlorophenyl)phenyl) pyrazole-4-carboxylate, ethyl 5-(2-morpholin-4-ylethoxy)-1-(4-(2-(2-methylpropanyl)phenyl)phenyl)-pyrazole-4-carboxylate, ethyl 5-(2-morpholin-4-ylethoxy)-1-(4-(2-propoxyphenyl)phenyl)pyrazole-4-carboxylate, ethyl 5-(2-morpholin-4-ylethoxy)-1-(4-(2-hydroxmethylphenyl) phenyl)pyrazole-4-carboxylate, ethyl 5-(2-morpholin-4-ylethoxy)-1-(4-(2-ethoxyphenyl)phenyl)pyrazole-4-carboxylate; ethyl 5-(2-morpholin-4-ylethoxy)-1-(4-(2-hydroxyethoxyphenyl)phenyl)-pyrazole-4-carboxylate, ethyl 5-(2-morpholin-4-ylethoxy)-1-(4-(2-nitrophenyl) phenyl)pyrazole-4-carboxylate, ethyl 5-(2-morpholinylethoxy)-1-(4-(2-acetoxynitrilephenyl)phenyl) pyrazole4-carboxylate, ethyl 5-(2-morpholin-4-ylethoxy)-1-(4-(2,3-dichlorophenyl)phenyl)pyrazole-4-carboxylate, 5-(2-morpholin-4-ylethoxy)-1-(4-isopropylphenyl) pyrazole-4-(1-methyl)tetrazole, 5-(2-morpholin-4-ylethoxy)-1-(4-isopropylphenyl)pyrazole-4-(2-methyl)-tetrazole, 5-(2-morpholin-4-ylethoxy)-1-(4-isopropylphenyl)pyrazole-4-(1-ethyl)-tetrazole, and 5-(2-morpholin-4-ylethoxy)-1-(4-isopropylphenyl)pyrazole-4-(2-ethyl)-tetrazole,5-(2-morpholin-4-ylethoxy)-1-[4-(2,6-dichlorophenyl)phenyl]pyrazole-4-(1-ethyl)-tetrazole, and 5-(2 -morpholin-4-ylethoxy)-1-[4-(2,6-dichlorophenyl) phenyl]pyrazole-4-(2ethyl)-tetrazole, 5-(2-morpholin -4-ylethoxy)-1-(4-isopropylphenyl)pyrazole-4-(2-methyl)-tetrazole, 5-(2-morpholin-4-ylethoxy )-1-(4-isopropylphenyl)pyrazole-4-(2-methyl)-tetrazole, (R)-(−)-5-(2-morpholin-4-ylethoxy)-1-[4-(2,6-dichlorophenyl) phenyl]pyrazole-4-(5-methyl)oxazoline, and (S)-(+)-5-(2-morpholin-4ylethoxy)-1-[4-(2,6-dichlorophenyl)phenyl] pyrazole-4-(5-methyl)oxazoline.

Even more preferred compounds useful in the present invention include ethyl 5-(2-morpholin-4-ylethoxy)-1-(4-(2-methoxymethoxyphenyl)phenyl)-pyrazole-4-carboxylate, ethyl 5-(2-morpholin-4-ylethoxy)-1-(4-(2,6-dichlorophenyl) phenyl)pyrazole-4-carboxylate, ethyl 5-(2-morpholin-4-ylethoxy)-1-(4-(2,3-dichlorophenyl)phenyl)pyrazole-4-carboxylate, 5-(2-morpholin-4-ylethoxy)-1-(4-isopropylphenyl)pyrazole-4-(1-methyl)-tetrazole, 5-(2-morpholin-4-ylethoxy)-1-(4-isopropylphenyl)pyrazole-4-(2-methyl)-tetrazole, ethyl 5-(2-morpholin-4-ylethoxy)-1-(4-(2-nitrophenyl)phenyl)pyrazole-4-carboxylate, 5-(2-morpholin-4-ylethoxy)-1-(4-isopropylphenyl)pyrazole-4-(1-ethyl)-tetrazole, and 5-(2-morpholin-4-ylethoxy)-1-(4-isopropylphenyl)pyrazole-4-(2-ethyl)-tetrazole, 5-(2-morpholin-4-ylethoxy)-1-[4-(2,6-dichlorophenyl)phenyl] pyrazole-4-(1-ethyl)-tetrazole, and 5-(2-morpholin-4-ylethoxy)-1-[4-(2,6-dichlorophenyl)phenyl]pyrazole-4-(2-ethyl)-tetrazole, 5-(2-morpholin-4-ylethoxy)-1-(4-isopropylphenyl)pyrazole-4-(1-methyl)-tetrazole, and 5-(2-morpholin-4-ylethoxy)-1-(4-isopropylphenyl)pyrazole-4-(2-methyl)-tetrazole.

The most preferred compounds useful in the present invention include ethyl 5-(2-morpholin-4-ylethoxy)-1-(4-(2-methoxymethoxyphenyl)phenyl)-pyrazole-4-carboxylate, ethyl 5-(2-morpholin-4-ylethoxy)-1-(4-(2,6-dichlorophenyl) phenyl)pyrazole-4-carboxylate, 5-(2-morpholin-4-ylethoxy)-1-(4-isopropylphenyl)pyrazole-4-(1-ethyl)-tetrazole, and 5-(2-morpholin-4-ylethoxy)-1-(4-isopropylphenyl)pyrazole-4-(2-ethyl)-tetrazole, 5-(2-morpholin-4-ylethoxy)-1-[4-(2,6-dichlorophenyl)phenyl] pyrazole-4-(1-ethyl )-tetrazole, 5-(2-morpholin-4-ylethoxy)-1-[4-(2,6-dichlorophenyl)phenyl]pyrazole-4-(2-ethyl)-tetrazole, 5-(2-morpholin-4-ylethoxy)-1-(4-isopropylphenyl)pyrazole-4-(1-methyl)-tetrazole, and 5-(2-morpholin-4-ylethoxy)-1-(4-isopropylphenyl)pyrazole-4-(2-methyl)-tetrazole.

The present invention provides compounds of Formula (I) above:

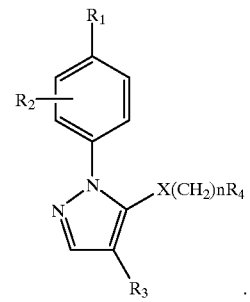

which can be prepared by a process which comprises:

a) reacting a hydrazine (2), wherein $R_1$ and $R_2$ are defined as above, (2)

[Structure: phenyl ring with R$_1$ at para position, R$_2$ substituent, and NH-NH$_2$ group]

with diethyl ethoxymethylenemalonate (3)

(3)

$$CH_3CH_2O-CH=C(CO_2CH_2CH_3)_2$$

in the presence of a base such as potassium carbonate in aqueous solution to form a compound of Formula (4).

(4)

[Structure: pyrazolone with R$_1$, R$_2$-substituted phenyl on N, and CO$_2$Et group]

Mitsunobu reaction of the compound of Formula (4) with N-hydroxyethyl morpholine (5)

(5)

[Structure: HO-CH$_2$CH$_2$-N-morpholine]

in the presence of triphenylphosphine and diisopropyl azodicarboxylate in a suitable solvent such as tetrahydrofuran provides a compound of Formula (I), wherein R$_3$ is ethoxycarbonyl group, X is 0, n is 2 and R$_4$ is morpholine.

b) Alternatively, in a second synthetic route of the present invention, the product of the Misunobu reaction above is saponified with a base such as NaOH in a mixture of ethanol and water followed by treatment of the resulting acid with oxalyl chloride in a suitable solvent such as benzene in presence of a catalytic amount of N,N'-dimethylformamide to afford an acid chloride of Formula (6)

(6)

[Structure: pyrazole with R$_1$, R$_2$-substituted phenyl on N, O-CH$_2$CH$_2$-morpholine, and COCl group]

Reaction of the acid chloride of Formula (6) with an amino alcohol of Formula (7), wherein R is C$_{1-6}$alkyl, (7)

[Structure: R-CH(OH)-CH$_2$-NH$_2$]

in a suitable solvent such as tetrahydrofuran provides an oxazoline of Formula (8).

(8)

[Structure: pyrazole with R$_1$, R$_2$-substituted phenyl on N, O-CH$_2$CH$_2$-morpholine, and oxazoline ring with R substituent]

Oxidation of the oxazoline of Formula (8) with an oxidant such as 2,3-dichloro-5,6-dicyano-1,4-benzoquinone ("DDQ") or triphenylphosphine-iodine affords an oxazole of Formula (I), where R$_3$ is an oxazolyl moiety, X is 0, n is 2 and R$_4$ is morpholine.

c) In a third embodiment of the present invention, treatment of a hydrazine of Formula (2) with ethyl (ethoxyethylene)cyanoacetate of Formula (9)

(9)

$$CH_3CH_2O-CH=C(CO_2CH_2CH_3)(CN)$$

in the presence of a base such as potassium carbonate in aqueous solution provides a compound of Formula (10).

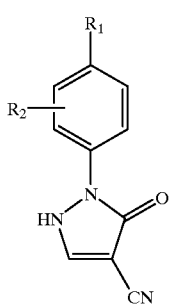

(10)

Alkylation of the compound of Formula (10) with an alkyl halide such as 1-chloro-2-(4-morpholinyl)ethane in presence of a base such as potassium carbonate in a suitable solvent such as tetrahydrofuran affords a compound of Formula (11).

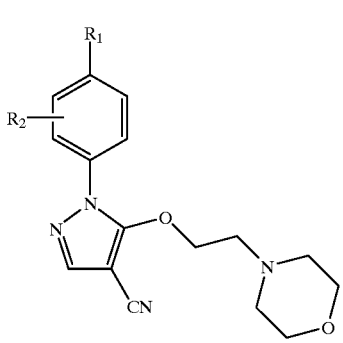

(11)

Reaction of the nitrile of Formula (11) with trimethyltin azide in a suitable solvent such as toluene followed by acidic treatment with hydrochloric acid in methanol provides a tetrazole of Formula (12).

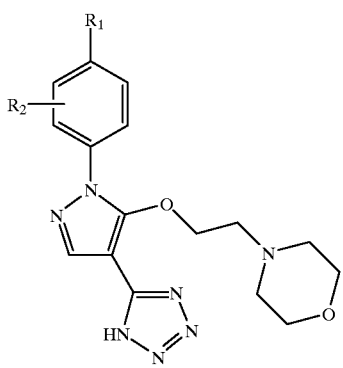

(12)

Alkylation of the tetrazole of Formula (12) with an alkyl halide such as ethyl iodide affords a mixture of ethyl tetrazoles of Formula (I), where $R_3$ is ethyl tetrazolyl moiety, X is O, n is 2 and $R_4$ is morpholine.

With appropriate manipulation and protection of any chemical functionalities, synthesis of the remaining compounds of Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

As used herein, "modulator" means both antagonist and agonist. Preferably the present modulators are antagonists.

As used herein, "treatment" of a disease includes, but is not limited to prevention, retardation and prophylaxis of the disease.

In addition to the conditions listed hereinabove, the present compounds are useful for the treatment of diseases including but not limited to immunologically-mediated inflammatory diseases such as rheumatoid arthritis, systemic lupus erythematosus, psoriasis, multiple schlerosis, diabetis and thyroiditis. In addition, the present compounds modulate bone formation/resorption and are useful in the treatment of conditions including but not limited to ankylosing spondylitis, gout, arthritis associated with gout, osteoarthritis and osteoporosis.

Compounds of Formula (I) and their pharmaceutically acceptable salts may be administered in a standard manner for the treatment of the indicated diseases, for example orally, parentarally, sub-lingually, dermally, transdermally, rectally, via inhalation or via buccal administration.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula(I) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula(I) or a pharmaceutically acceptable salt thereof calculated as the free acid. the daily dosage regimen for parenteral administration is suitably about 0.001 mg/Kg to 40 mg/Kg, of a compound of Formula (I) or a pharmaceutically acceptable salt thereof calculated as the free acid. the daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following tests:

Human CB2 Cannabinoid Receptor Binding Assay

HEK 293 cells, stably transfected with the human CB2 receptor are scaled up as follows. CB2 membrane is made from polyclonal CB2 receptors expressing 293 cells. The assay buffer comprises 50 mM Tris (pH 7.5), 5 mM MgCl2, 2.5 mM EDTA and 5 mg/ml fatty-acid free Bovine Serum Albumin. All chemicals utilized are obtained from Sigma, except fatty acid-free Bovine Albumin Fraction V, which is from CalBiochem, and tritiated 5-(1,1-dimethylheptyl)-2-(5-hydroxypropyl)cyclohexyl)-1 alpha, 2 beta, 5 alpha)-phenol ("$^3$H-CP 55,940") (103.4 Ci/mmol, 1 m Ci/ml), which is from DuPont NEN. All compounds are dissolved in DMSO.

The final compound concentrations range from 1.00 $E^{-4}$ to 1.00$E^{-10}$. The reaction mixture is obtained by combining 1.3–1.8 nM $^3$H-CP 55,940, in a reaction volume of 150 $\mu$l, and 50 $\mu$g membrane in homogenization buffer containing fatty acid-free BSA. A 96 deep well microtiter polypropylene plate is utilized. 50 $\mu$l $^3$H-CP 55,940 stock solution are added three times to each well of the microtiter plate. 45 $\mu$l assay buffer are added to the total number of binding samples, followed by 45 $\mu$l of 1 $\mu$M cold $^3$H-CP 55,940 to non-specific samples. 5 $\mu$l of each concentration of compound are added to the 96 deep well plate except the designated total and non-specific wells. 5 $\mu$l DMSO are added manually for the total and non-specific wells.

The binding reaction is initiated by the addition of 50 $\mu$l of 20 $\mu$g per well of CB2 membrane. The reaction mixture is incubated for one hour at 30° C. in a shaking water bath. The binding reaction is terminated by rapid filtration onto GF/B filter paper treated with wash buffer using a Brandel 96-well cell harvester, followed by washing five times with 3 ml ice-cold wash buffer. The filters are air dried, placed in scintillation fluid and $^3$H-CP 55,940 radioactivity determined by liquid scintillation counting. Competition binding curves are analyzed by non-linear regression using GRAPHPAD PRISM. $K_i$ values ranging from 25 nM to 10 $\mu$M are obtained for the antagonists of the present invention.

The following examples are illustrative, but not limiting of the embodiments of the present invention.

EXAMPLE 1

Ethyl 5-(2-morpholin-4-ylethoxy)-1-[4-(2-formylphenyl)phenyl]pyrazole-4-carboxylate a) Ethyl 1-(4-bromophenyl)-4-pyrazolin-5-one carboxylate A solution of 4-bromophenylhydrazine hydrochloride (15.00 g, 0.07 mol), potassium carbonate (30.00 g, 0.20 mol) and diethyl ethoxymethylene malonate (20.00 ml, 0.08 mol) in water (250 mL) was stirred at reflux for 18 h. Extraction with ethyl acetate (3×100 mL), washing the combined organics with 10% HCl solution, gave a crude oil. Purification by flash chromatography of the oil (silica gel, 25% ethyl acetate/hexane) afforded the title compound as a brown solid (19.70 g, 93%). $^1$H NMR (250 MHz, CDCl$_3$) d 7.74 (s, 1H), 7.58–7.62 (d, 1H), 7.36–7.42 (d, 1H), 5.35 (s, 1H), 4.40 (q, 2H), 1.33 (t, 3H). MS(ESI) m/e 311.1 [M+H]$^+$; mp: 164° C. (methanol).

b) Ethyl 5-(2-morpholin-4-ylethoxy)-1-(4-bromophenyl)pyrazole-4-carboxylate

A solution of ethyl 1-(4-bromophenyl)-4-pyrazolin-5-one carboxylate (18.10 g, 0.06 mol), triphenylphosphine (20.00 g, 0.08 mol), diisopropyl azodicarboxylate (15.00 $\mu$L, 0.08 mol) and 4-(2-hydroxyethyl)morpholine (8.50 mL, 0.07 mol) in THF (250 mL) was stirred at reflux for 5 h. The reaction was quenched with water and extracted with ethyl acetate. The organic extract was washed with brine and dried (Na$_2$SO$_4$). After removing the solvent, flash chromatography of the residue (silica gel, 50% ethyl acetate/hexane) afforded the title compound as a brown oil (19.50 g, 79%). $^1$H NMR (250 MHz, CDCl$_3$) d 7.90 (s, 1H), 7.62 (d, 1H), 7.52 (d, 1H), 4.55 (t, 2H), 4.35 (q, 2H), 3.52 (t, 4H), 2.61 (t, 2H), 2.28 (t, 4H), 1.35 (t, 3H). MS(ESI) m/e 424.3 [M+H]$^+$.

c) Ethyl 5-(2-morpholin-4-ylethoxy)-1-[4-(2-formylphenyl)phenyl]pyrazole-4-carboxylate A mixture of ethyl 5-(2-morpholin-4-ylethoxy)-1-(4-bromophenyl)pyrazole-4-carboxylate (0.25 g, 0.59 mmol), sodium carbonate (0.20 g, 1.77 mmol), tetrakis(triphenylphosphine) palladium (0) (0.12 g, 0.18 mmol) and 1-formylbenzeneboronic acid (0.10 g, 0.76 mmol) in a solution of toluene (10 mL), ethanol (1 mL) and water (1 mL) was stirred at reflux for 18 h. The reaction was diluted with water and extracted with ethyl acetate. The organic extract was washed with brine and dried (Na$_2$SO$_4$). After removing the solvent, flash chromatography of the residue (silica gel, 50% ethyl acetate/hexane) afforded the title compound as an oil (0.14 g, 66%). $^1$H NMR (250 MHz, CDCl$_3$) d 9.98 (s, 1H), 8.01 (d, 1H), 7.92 (s, 1H), 7.85 (d, 2H), 7.62 (d, 1H), 7.46 (m, 4H), 4.65 (t, 2H), 4.35 (q, 2H), 3.56 (t, 4H), 2.68 (t, 2H), 2.38 (t, 4H), 1.38 (t, 3H). MS(ESI) m/e 450.4 [M+H]$^+$.

EXAMPLES 2–63

The following compounds are synthesized according to the methods of Example 1:

ethyl 5-(2-morpholin-4-ylethoxy)-1-(4-(2-formylphenyl)phenyl)pyrazole-4-carboxylate, ethyl 5-(2-morpholin-4-ylethoxy)-1-(4-naphthylphenyl)pyrazole-4-carboxylate, ethyl 5-(2-morpholin-4-ylethoxy)-1-(4-(2-methoxymethoxyphenyl)phenyl)-pyrazole-4-carboxylate, ethyl 5-(2-morpholin-4-ylethoxy)-1-(4-(2-hydroxyphenyl)phenyl)pyrazole-4-carboxylate, ethyl 5-(2-morpholin-4-ylethoxy)-1-(4-(2,6-dimethylphenyl)phenyl)pyrazole-4-carboxylate, ethyl 5-(2-morpholin-4-ylethoxy)-1-(4-(2,6-dichlorophenyl)phenyl)pyrazole-4-carboxylate, ethyl 5-(2-morpholin-4-ylethoxy)-1-(4-(2-(2-methylpropanyl)phenyl)phenyl)-pyrazole-4-carboxylate, ethyl 5-(2-morpholin-4-ylethoxy)-1-(4-(2-propoxyphenyl)phenyl)pyrazole-4-carboxylate, ethyl 5-(2-morpholin-4-ylethoxy)-1-(4-(2-hydroxmethylphenyl)phenyl)pyrazole-4-carboxylate, ethyl 5-(2-morpholin-4-ylethoxy)-1-(4-(2-ethoxyphenyl)phenyl)pyrazole-4-carboxylate,
ethyl 5-(2-morpholin-4-ylethoxy)-1-(4-(2-hydroxyethoxyphenyl)phenyl)-pyrazole-4-carboxylate,
ethyl 5-(2-morpholin-4-ylethoxy)-1-(4-(2-nitrophenyl)phenyl)pyrazole-4-carboxylate,
ethyl 5-(2-morpholin-4-ylethoxy)-1-(4-(2-acetoxynitrilephenyl)phenyl)pyrazole-4-carboxylate,
ethyl 5-(2-morpholin-4-ylethoxy)-1-(4-(2,3-dichlorophenyl)phenyl)pyrazole-4-carboxylate,
5-(2-morpholin-4-ylethoxy)-1-(4-isopropylphenyl)pyrazole-4-(1-ethyl)-tetrazole,
5-(2-morpholin-4-ylethoxy)-1-(4-isopropylphenyl)pyrazole-4-(2-ethyl)-tetrazole,
5-(2-morpholin-4-ylethoxy)-1-(4-isopropylphenyl)pyrazole-4-carboxylic acid,
5-(2-morpholin-4-ylethoxy)-1-(4-isopropylphenyl)pyrazol-4-yl methanol,
5-(2-morpholin-4-ylethoxy)-1-(4-isopropylphenyl)pyrazole-4-N,N-dimethylcarbamidate,
5-(2-morpholin-4-ylethoxy)-1-(4-isopropylphenyl)pyrazole-4-carbamide,
(+/−)-ethyl 5-((1-methyl-2-piperidinyl)methoxy)-1-(4-isopropylphenyl)pyrazole-4-carboxylate,
5-(2-morpholin-4-ylethoxy)-1-(4-isopropylphenyl)pyrazole,
5-(2-morpholin-4-ylethoxy)-1-(4-isopropylphenyl)pyrazole-4-methyl, ethyl 5-(2-morpholin-4-ylethoxy)-1-(4-(3,5-bis(trifluoromethyl)phenyl)-phenyl)pyrazole-4-carboxylate,
ethyl 5-(2-morpholin-4-ylethoxy)-1-(4-phenylphenyl)pyrazole-4-carboxylate,
ethyl 5-(2-morpholin-4-ylethoxy)-1-(4-(3,5-dichlorophenyl)phenyl)pyrazole-4-carboxylate,
ethyl 5-(2-morpholin-4-ylethoxy)-1-(4-(3-chlorophenyl)phenyl)pyrazole-4-carboxylate,
ethyl 5-(2-morpholin-4-ylethoxy)-1-(4-(4-chlorophenyl)phenyl)pyrazole-4-carboxylate,
ethyl 5-(2-morpholin-4-ylethoxy)-1-(4-(4-formylphenyl)phenyl)pyrazole-4-carboxylate,
ethyl 5-(2-morpholin-4-ylethoxy)-1-(4-(2,4-dichlorophenyl)phenyl)pyrazole-4-carboxylate,
ethyl 5-(2-morpholin-4-ylethoxy)-1-(4-(4-methoxyphenyl)phenyl)pyrazole-4-carboxylate,
ethyl 5-(2-morpholin-4-ylethoxy)-1-(4-(4-methylphenyl)phenyl)pyrazole-4-carboxylate,
ethyl 5-(2-morpholin-4-ylethoxy)-1-(4-(3-aminophenyl)phenyl)pyrazole-4-carboxylate,
5-(2-morpholin-4-ylethoxy)-1-(4-(4-carboxyphenyl)phenyl)pyrazole-4-carboxylic acid,
methyl 5-(2-morpholin-4-ylethoxy)-1-(4-(4-methoxycarbonylphenyl)-phenyl)pyrazole-4-carboxylate,
ethyl 5-(2-morpholin-4-ylethoxy)-1-(4-(2-N-diethylacetamidephenyl)-phenyl)pyrazole-4-carboxylate,
ethyl 5-(2-morpholin-4-ylethoxy)-1-(4-(2-octoxyphenyl)phenyl)pyrazole-4-carboxylate,
ethyl 5-(2-morpholin-4-ylethoxy)-1-(4-(2-tert-butyloxycarbomethoxyphenyl)-phenyl)pyrazole-4-carboxylate,
ethyl 5-(2-morpholin-4-ylethoxy)-1-(4-(2-benzyloxyphenyl)phenyl)pyrazole-4-carboxylate,
5-(2-morpholin-4-ylethoxy)-1-(4-isopropylphenyl)pyrazole-4-methyl ketone,
5-(2-morpholin-4-ylethoxy)-1-(4-isopropylphenyl)pyrazol-4-yl-N-ethylcarboxamide,
ethyl 5-(2-morpholin-4-ylethoxy)-1-(4-(2-carbomethoxyphenyl)phenyl)pyrazole-4-carboxylate,
ethyl 5-(2-morpholin-4-ylethoxy)-1-(4-anthracenylphenyl)pyrazole-4-carboxylate,
ethyl 5-(2-morpholin-4-ylethoxy)-1-(4-(2-n-butoxyphenyl)phenyl)pyrazole-4-carboxylate,
ethyl 5-(2-morpholin-4-ylethoxy)-1-(4-(2-methoxyethoxyphenyl)phenyl)-pyrazole-4-carboxylate,
methyl 5-(2-morpholin-4-ylethoxy)-1-(4-isopropylphenyl)pyrazole-4-carboxylate,
isopropyl 5-(2-morpholin-4-ylethoxy)-1-(4-isopropylphenyl)pyrazole-4-carboxylate,
propyl 5-(2-morpholin-4-ylethoxy)-1-(4-isopropylphenyl)pyrazole-4-carboxylate,
ethyl 5-(2-pyridinylmethoxy)-1-(4-isopropylphenyl)pyrazole-4-carboxylate,
5-(2-morpholin-4-ylethoxy)-1-(4-isopropylphenyl)pyrazole-4-oxazoline,
5-(2-morpholin-4-ylethoxy)-1-(4-isopropylphenyl)pyrazole-4-(5-methyl)oxazoline,
5-(2-morpholin-4-ylethoxy)-1-(4-isopropylphenyl)pyrazole-4-(2-methyl)oxadiazole,
4-methoxymethyl-5-(2-morpholin-4-ylethoxy)-1-(4-(2-methylnaphthyl)phenyl)-pyrazole,
5-(2-morpholin-4-ylethoxy)-1-(4-(2,6-dichlorophenyl)phenyl)pyrazole,
5-(2-morpholin-4-ylethoxy)-1-(4-(2,3-dichlorophenyl)phenyl)pyrazole,
5-(2-morpholin-4-ylethoxy)-1-(4-isopropylphenyl)pyrazole-4-nitrile,
5-(2-morpholin-4-ylethoxy)-1-(4-isopropylphenyl)pyrazole-4-tetrazole,
a mixture of 5-(2-morpholin-4-ylethoxy)-1-(4-isopropylphenyl)pyrazole-4-(1-methyl)-tetrazole and 5-(2-morpholin-4-ylethoxy)-1-(4-isopropylphenyl)pyrazole-4-(2-methyl)-tetrazole,
ethyl 5-(4-pyridinylmethoxy)-1-(4-isopropylphenyl)pyrazole-4-carboxylate,
ethyl 5-(2-morpholin-4-ylethoxy)-1-(4-isopropylphenyl)pyrazole-4-carboxylate,
5-(2-morpholin-4-ylethoxy)-1-(4-isopropylphenyl)pyrazole-4-tetrazole,
a mixture of 5-(2-morpholin-4-ylethoxy)-1-(4-isopropylphenyl)pyrazole-4-(1-methyl)-tetrazole and 5-(2-morpholin-4-ylethoxy)-1-(4-isopropylphenyl)pyrazole-4-(2-methyl)-tetrazole,
ethyl 5-(4-pyridinylmethoxy)-1-(4-isopropylphenyl)pyrazole-4-carboxylate, and
ethyl 5-(2-morpholin-4-ylethoxy)-1-(4-isopropylphenyl)pyrazole-4-carboxylate.

Formulations for pharmaceutical use incorporating compounds of the present invention can be prepared in various forms and with numerous excipients. Examples of such formulations are given below.

EXAMPLE 64

Inhalant Formulation

A compound of Formula I, (1 mg to 100 mg) is aerosolized from a metered dose inhaler to deliver the desired amount of drug per use.

EXAMPLE 65

| Tablet Formulation | |
|---|---|
| Tablets/Ingredients | Per Tablet |
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for tablet formulation:
Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 66
Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound of formula (I):

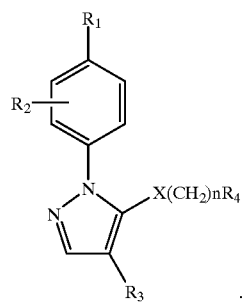

wherein:
R$_1$ is OCH$_3$, Br, isopropyl, or Ar;
R$_2$ is H, OH, C$_{1-5}$alkoxy, C$_{1-5}$alkyl, N(R$_5$)$_2$, NO$_2$, Br, F, I, Cl, CF$_3$, or X(C(R$_5$)$_2$)$_n$OR$_5$;
R$_3$ is hydrogen, (CH$_2$)$_n$XR$_5$, C(O)R$_5$, CO$_2$R$_5$, CON(R$_5$)$_2$, oxazolinyl, oxazolyl, thiazolyl, pyrazolyl, triazolyl, imidazolyl, tetrazolyl, imidazolinyl, thiazolinyl, isoxazolyl, oxadiazolyl, or thiadiazolyl, each of these heterocyclic rings being unsubstituted or substituted by one or two C$_{1-3}$ alkyl or fluoroalkyl groups;
R$_4$ is morpholinyl, piperazinyl or piperidinyl, each moiety being unsubstituted or substituted by one or two C$_{1-5}$alkyl, OH, NO$_2$ or N(R$_5$)$_2$ groups;

R$_5$ is hydrogen or C$_{1-8}$alkyl;
X is O or NR$_5$;
Ar is phenyl, anthracenyl, naphthyl, indolyl, pyridinyl, thiophenyl, thiazolyl, isothiazolyl, triazolyl, tetrazolyl, imidazolyl, oxadiazolyl, pyrrolyl or pyrimidinyl; each moiety being unsubstituted or substituted by one or two Z groups;
Z is H, OH, CO$_2$R$_5$, C$_{1-10}$alkoxy, C$_{1-5}$alkyl, N(R$_5$)$_2$, NO$_2$, Br, F, I, Cl, CF$_3$, or X(CH$_2$)$_n$OR$_5$; and
n is 1 to 6; and
pharmaceutically acceptable salts thereof;
provided that when n is 1, R$_5$ is not hydrogen in X(CH$_2$)$_n$OR$_5$.

2. A compound according to claim 1 wherein:
R$_1$ is C$_{1-5}$ alkyl or Ar;
R$_2$ is hydrogen, C$_{1-5}$ alkyl or Ar;
R$_3$ is selected from the group consisting of CO$_2$R$_5$, oxazolinyl, tetrazolyl, and oxazolyl, unsubstituted or substituted by one or two C$_{1-2}$ alkyl or fluoroalkyl groups;
R$_4$ is morpholinyl, piperazinyl or piperidinyl, unsubstituted or substituted by one or two C$_{1-5}$ alkyl groups;
R$_5$ is C$_{1-5}$ alkyl;
X is O;
Ar is phenyl, unsubstituted or substituted by one or two Z groups; and
n is 2.

3. A compound according to claim 1 wherein:
R$_1$ is isopropyl or phenyl substituted by dichloro, CHO, OCH$_2$OCH$_3$; and
R$_5$ is methyl or ethyl.

4. A compound according to claim 1 selected from the group consisting of:
ethyl 5-(2-morpholin-4-ylethoxy)-1-(4-(2-formylphenyl)phenyl)pyrazole-4-carboxylate,
ethyl 5-(2-morpholin-4-ylethoxy)-1-(4-naphthylphenyl)pyrazole-4-carboxylate,
ethyl 5-(2-morpholin-4-ylethoxy)-1-(4-(2-methoxymethoxyphenyl)phenyl)-pyrazole-4-carboxylate,
ethyl 5-(2-morpholin-4-ylethoxy)-1-(4-(2-hydroxyphenyl)phenyl)pyrazole-4-carboxylate,
ethyl 5-(2-morpholin-4-ylethoxy)-1-(4-(2,6-dimethylphenyl)phenyl)pyrazole-4-carboxylate,
ethyl 5-(2-morpholin-4-ylethoxy)-1-(4-(2,6-dichlorophenyl)phenyl)pyrazole-4-carboxylate,
ethyl 5-(2-morpholin-4-ylethoxy)-1-(4-(2-(2-methylpropanyl)phenyl)phenyl)-pyrazole-4-carboxylate,
ethyl 5-(2-morpholin-4-ylethoxy)-1-(4-(2-propoxyphenyl)phenyl)pyrazole-4-carboxylate,
ethyl 5-(2-morpholin-4-ylethoxy)-1-(4-(2-hydroxmethylphenyl)phenyl)pyrazole-4-carboxylate,
ethyl 5-(2-morpholin-4-ylethoxy)-1-(4-(2-ethoxyphenyl)phenyl)pyrazole-4-carboxylate,
ethyl 5-(2-morpholin-4-ylethoxy)-1-(4-(2-hydroxyethoxyphenyl)phenyl)-pyrazole-4-carboxylate,
ethyl 5-(2-morpholin-4-ylethoxy)-1-(4-(2-nitrophenyl)phenyl)pyrazole-4-carboxylate,
ethyl 5-(2-morpholin-4-ylethoxy)-1-(4-(2-acetoxynitrilephenyl)phenyl)pyrazole-4-carboxylate, ethyl 5-(2-morpholin-4-ylethoxy)-1-(4-(2,3-dichlorophenyl)phenyl)pyrazole-4-carboxylate,
5-(2-morpholin-4-ylethoxy)-1-(4-isopropylphenyl)pyrazole-4-(1-ethyl)-tetrazole,
5-(2-morpholin-4-ylethoxy)-1-(4-isopropylphenyl)pyrazole-4-(2-ethyl)-tetrazole,
5-(2-morpholin-4-ylethoxy)-1-(4-isopropylphenyl)pyrazole-4-carboxylic acid,
5-(2-morpholin-4-ylethoxy)-1-(4-isopropylphenyl)pyrazol-4-yl methanol,
5-(2-morpholin-4-ylethoxy)-1-(4-isopropylphenyl)pyrazole-4-N,N-dimethylcarbamidate,
5-(2-morpholin-4-ylethoxy)-1-(4-isopropylphenyl)pyrazole-4-carbamide,
(+/−)-ethyl 5-((1-methyl-2-piperidinyl)methoxy)-1-(4-isopropylphenyl)pyrazole-4-carboxylate,
5-(2-morpholin-4-ylethoxy)-1-(4-isopropylphenyl)pyrazole,
5-(2-morpholin-4-ylethoxy)-1-(4-isopropylphenyl)pyrazole-4-methyl,
ethyl 5-(2-morpholin-4-ylethoxy)-1-(4-(3,5-bis(trifluoromethyl)phenyl)-phenyl)pyrazole-4-carboxylate,
ethyl 5-(2-morpholin-4-ylethoxy)-1-(4-phenylphenyl)pyrazole-4-carboxylate,
ethyl 5-(2-morpholin-4-ylethoxy)-1-(4-(3,5-dichlorophenyl)phenyl)pyrazole-4-carboxylate,
ethyl 5-(2-morpholin-4-ylethoxy)-1-(4-(3-chlorophenyl)phenyl)pyrazole-4-carboxylate,
ethyl 5-(2-morpholin-4-ylethoxy)-1-(4-(4-chlorophenyl)phenyl)pyrazole-4-carboxylate,
ethyl 5-(2-morpholin-4-ylethoxy)-1-(4-(4-formylphenyl)phenyl)pyrazole-4-carboxylate,
ethyl 5-(2-morpholin-4-ylethoxy)-1-(4-(2,4-dichlorophenyl)phenyl)pyrazole-4-carboxylate,
ethyl 5-(2-morpholin-4-ylethoxy)-1-(4-(4-methoxyphenyl)phenyl)pyrazole-4-carboxylate,
ethyl 5-(2-morpholin-4-ylethoxy)-1-(4-(4-methylphenyl)phenyl)pyrazole-4-carboxylate,
ethyl 5-(2-morpholin-4-ylethoxy)-1-(4-(3-aminophenyl)phenyl)pyrazole-4-carboxylate,
5-(2-morpholin-4-ylethoxy)-1-(4-(4-carboxyphenyl)phenyl)pyrazole-4-carboxylic acid,
methyl 5-(2-morpholin-4-ylethoxy)-1-(4-(4-methoxycarbonylphenyl)-phenyl)pyrazole-4-carboxylate,
ethyl 5-(2-morpholin-4-ylethoxy)-1-(4-(2-N-diethylacetamidephenyl)-phenyl)pyrazole-4-carboxylate,
ethyl 5-(2-morpholin-4-ylethoxy)-1-(4-(2-octoxyphenyl)phenyl)pyrazole-4-carboxylate,
ethyl 5-(2-morpholin-4-ylethoxy)-1-(4-(2-tert-butyloxycarbomethoxyphenyl)-phenyl)pyrazole-4-carboxylate,
ethyl 5-(2-morpholin-4-ylethoxy)-1-(4-(2-benzyloxyphenyl)phenyl)pyrazole-4-carboxylate,
5-(2-morpholin-4-ylethoxy)-1-(4-isopropylphenyl)pyrazole-4-methyl ketone,
5-(2-morpholin-4-ylethoxy)-1-(4-isopropylphenyl)pyrazol-4-yl-N-ethylcarboxamide,
ethyl 5-(2-morpholin-4-ylethoxy)-1-(4-(2-carbomethoxyphenyl)phenyl)pyrazole-4-carboxylate,
ethyl 5-(2-morpholin-4-ylethoxy)-1-(4-anthracenylphenyl)pyrazole-4-carboxylate,
ethyl 5-(2-morpholin-4-ylethoxy)-1-(4-(2-n-butoxyphenyl)phenyl)pyrazole-4-carboxylate,
ethyl 5-(2-morpholin-4-ylethoxy)-1-(4-(2-methoxyethoxyphenyl)phenyl)-pyrazole-4-carboxylate,
methyl 5-(2-morpholin-4-ylethoxy)-1-(4-isopropylphenyl)pyrazole-4-carboxylate,
isopropyl 5-(2-morpholin-4-ylethoxy)-1-(4-isopropylphenyl)pyrazole-4-carboxylate,
propyl 5-(2-morpholin-4-ylethoxy)-1-(4-isopropylphenyl)pyrazole-4-carboxylate,
5-(2-morpholin-4-ylethoxy)-1-(4-isopropylphenyl)pyrazole-4-oxazoline,
5-(2-morpholin-4-ylethoxy)-1-(4-isopropylphenyl)pyrazole-4-(5-methyl)oxazoline,
(R)-(−)-5-(2-morpholin-4-ylethoxy)-1-[4-(2,6-dichlorophenyl)phenyl]pyrazole-4-(5-methyl)oxazoline, (S)-(+)-5-(2-morpholin-4-ylethoxy)-1-[4-(2,6-dichlorophenyl)phenyl]pyrazole-4-(5-methyl)oxazoline, 5-(2-morpholin-4-ylethoxy)-1-(4-isopropylphenyl)pyrazole-4-(2-methyl)oxadiazole,
4-methoxymethyl-5-(2-morpholin-4-ylethoxy)-1-(4-(2-methylnaphthyl)phenyl)-pyrazole,
5-(2-morpholin-4-ylethoxy)-1-(4-(2,6-dichlorophenyl)phenyl)pyrazole,
5-(2-morpholin-4-ylethoxy)-1-(4-(2,3-dichlorophenyl)phenyl)pyrazole,
5-(2-morpholin-4-ylethoxy)-1-(4-isopropylphenyl)pyrazole-4-nitrile,
5-(2-morpholin-4-ylethoxy)-1-(4-isopropylphenyl)pyrazole-4-tetrazole,
5-(2-morpholin-4-ylethoxy)-1-(4-isopropylphenyl)pyrazole-4-(1-methyl)-tetrazole,
5-(2-morpholin-4-ylethoxy)-1-(4-isopropylphenyl)pyrazole-4-(2-methyl)-tetrazole,
ethyl 5-(2-morpholin-4-ylethoxy)-1-(4-isopropylphenyl)pyrazole-4-carboxylate,
5-(2-morpholin-4-ylethoxy)-1-[4-(2,6-dichlorophenyl)phenyl]pyrazole-4-(1-methyl)-tetrazole, 5-(2-morpholin-4-ylethoxy)-1-[4-(2,6-dichlorophenyl)phenyl]pyrazole-4-(2-methyl)-tetrazole, and ethyl 5-(2-morpholin-4-ylethoxy)-1-(4-isopropylphenyl)pyrazole-4-carboxylate.

5. A compound according to claim 1 selected from the group consisting of:
ethyl 5-(2-morpholin-4-ylethoxy)-1-(4-(2-formylphenyl)phenyl)pyrazole-4-carboxylate,
ethyl 5-(2-morpholin-4-ylethoxy)-1-(4-(2-methoxymethoxyphenyl)phenyl)-pyrazole-4-carboxylate,
ethyl 5-(2-morpholin-4-ylethoxy)-1-(4-(2-hydroxyphenyl)phenyl)pyrazole-4-carboxylate,
ethyl 5-(2-morpholin-4-ylethoxy)-1-(4-(2,6-dimethylphenyl)phenyl)pyrazole-4-carboxylate;
ethyl 5-(2-morpholin-4-ylethoxy)-1-(4-(2,6-dichlorophenyl)phenyl)pyrazole-4-carboxylate,
ethyl 5-(2-morpholin-4-ylethoxy)-1-(4-(2-(2-methylpropanyl)phenyl)phenyl)-pyrazole-4-carboxylate,
ethyl 5-(2-morpholin-4-ylethoxy)-1-(4-(2-propoxyphenyl)phenyl)pyrazole-4-carboxylate, ethyl 5-(2-morpholin-4-ylethoxy)-1-(4-(2-hydroxmethylphenyl)phenyl)pyrazole-4-carboxylate, ethyl 5-(2-morpholin-4-ylethoxy)-1-(4-(2-ethoxyphenyl)phenyl)pyrazole-4-carboxylate;

ethyl 5-(2-morpholin-4-ylethoxy)-1-(4-(2-hydroxyethoxyphenyl)phenyl)-pyrazole-4-carboxylate, ethyl 5-(2-morpholin-4-ylethoxy)-1-(4-(2-nitrophenyl)phenyl)pyrazole-4-carboxylate, ethyl 5-(2-morpholin-4-ylethoxy)-1-(4-(2-acetoxynitrilephenyl)phenyl)pyrazole-4-carboxylate, ethyl 5-(2-morpholin-4-ylethoxy)-1-(4-(2,3-dichlorophenyl)phenyl)pyrazole-4-carboxylate, 5-(2-morpholin-4-ylethoxy)-1-(4-isopropylphenyl)pyrazole-4-(1-methyl)-tetrazole, 5-(2-morpholin-4-ylethoxy)-1-(4-isopropylphenyl)pyrazole-4-(2-methyl)-tetrazole, 5-(2-morpholin-4-ylethoxy)-1-(4-isopropylphenyl)pyrazole-4-(1-ethyl)-tetrazole, and 5-(2-morpholin-4-ylethoxy)-1-(4-isopropylphenyl)pyrazole-4-(2-ethyl)-tetrazole.

6. A compound according to claim 1 selected from the group consisting of:

ethyl 5-(2-morpholin-4-ylethoxy)-1-(4-(2-methoxymethoxyphenyl)phenyl)-pyrazole-4-carboxylate, ethyl 5-(2-morpholin-4-ylethoxy)-1-(4-(2,6-dichlorophenyl)phenyl)pyrazole-4-carboxylate, ethyl 5-(2-morpholin-4-ylethoxy)-1-(4-(2,3-dichlorophenyl)phenyl)pyrazole-4-carboxylate, 5-(2-morpholin-4-ylethoxy)-1-(4-isopropylphenyl)pyrazole-4-(1-methyl)-tetrazole, 5-(2-morpholin-4-ylethoxy)-1-(4-isopropylphenyl)pyrazole-4-(2-methyl)-tetrazole, ethyl 5-(2-morpholin-4-ylethoxy)-1-(4-(2-nitrophenyl)phenyl)pyrazole-4-carboxylate, 5-(2-morpholin-4-ylethoxy)-1-[4-(2,6-dichlorophenyl)phenyl]pyrazole-4-(1-ethyl)-tetrazole, and 5-(2-morpholin-4-ylethoxy)-1-[4-(2,6-dichlorophenyl)phenyl]pyrazole-4-(2-ethyl)-tetrazole.

7. A compound according to claim 1 selected from the group consisting of:

ethyl 5-(2-morpholin-4-ylethoxy)-1-(4-(2-methoxymethoxyphenyl)phenyl)-pyrazole-4-carboxylate, ethyl 5-(2-morpholin-4-ylethoxy)-1-(4-(2,6-dichlorophenyl)phenyl)pyrazole-4-carboxylate, 5-(2-morpholin-4-ylethoxy)-1-(4-isopropylphenyl)pyrazole-4-(1-ethyl)-tetrazole, and 5-(2-morpholin-4-ylethoxy)-1-(4-isopropylphenyl)pyrazole-4-(2-ethyl)-tetrazole.

8. A pharmaceutical composition comprising a compound according to claim 1 and a pharmaceutically acceptable carrier.

9. A method of antagonizing cannabinoid 2 receptors which comprises administering to a subject in need thereof, an effective amount of a compound of claim 1.

10. A method of treatment of diseases caused by an excess of cannabinoid comprising administering to a subject in need thereof an effective amount of a cannabinoid receptor 2 antagonist according to claim 1.

11. A method of treating an immunologically-mediated inflammatory disease selected from the group consisting of rheumatoid arthritis, systemic lupus erythematosus, psoriasis, multiple sclerosis, diabetes and thyroiditis which comprises administering to a subject in need thereof an effective amount of a compound according to claim 1.

12. A method of treating a disease selected from the group consisting of ankylosing spondylitis, gout, gouty arthritis, osteoarthritis and osteoporosis which comprises administering to a subject in need thereof an effective amount of a compound according to claim 1.

13. A method of treating renal ischemia which comprises administering to a subject in need thereof an effective amount of a compound according to claim 1.

* * * * *